United States Patent [19]
Graf

[11] Patent Number: 5,562,737
[45] Date of Patent: Oct. 8, 1996

[54] EXTRA-DISCAL INTERVERTEBRAL PROSTHESIS

[76] Inventor: Henry Graf, 8, rue Duquesne, Lyon, France, 69006

[21] Appl. No.: 340,887

[22] Filed: Nov. 15, 1994

[30] Foreign Application Priority Data

Nov. 18, 1993 [FR] France .................................. 93 14024

[51] Int. Cl.⁶ ........................................................ A61F 2/44
[52] U.S. Cl. ................................................ 623/17; 606/61
[58] Field of Search ........................ 623/17; 606/54–59, 606/60, 61, 71

[56] References Cited

U.S. PATENT DOCUMENTS

| | | | |
|---|---|---|---|
| 2,238,870 | 4/1941 | Haynes | 606/59 |
| 2,346,346 | 4/1944 | Anderson | 606/59 |
| 4,135,505 | 1/1979 | Day | 606/57 |
| 4,312,336 | 1/1982 | Danieletto et al. | 606/57 |
| 4,621,627 | 11/1986 | De Bastiani et al. | 606/57 |
| 5,092,867 | 3/1992 | Harms et al. | 606/61 |
| 5,304,177 | 4/1994 | Pennig | 606/58 |
| 5,320,622 | 6/1994 | Faccioli et al. | 606/58 |
| 5,375,823 | 12/1994 | Navas | 267/195 |

FOREIGN PATENT DOCUMENTS

| | | | |
|---|---|---|---|
| 516567 | 12/1992 | European Pat. Off. | 606/61 |
| 2697428 | 5/1994 | France | 606/61 |

*Primary Examiner*—Michael J. Milano
*Attorney, Agent, or Firm*—Dowell & Dowell

[57] ABSTRACT

An extra-discal intervertebral prosthesis comprising at least a partially closed, elongated body including a compression chamber having an elastic block at one end. The block has a free face abutted by a ball joint associated with a first of two fixation means engagable in spaced vertebrae of a patient.

32 Claims, 11 Drawing Sheets

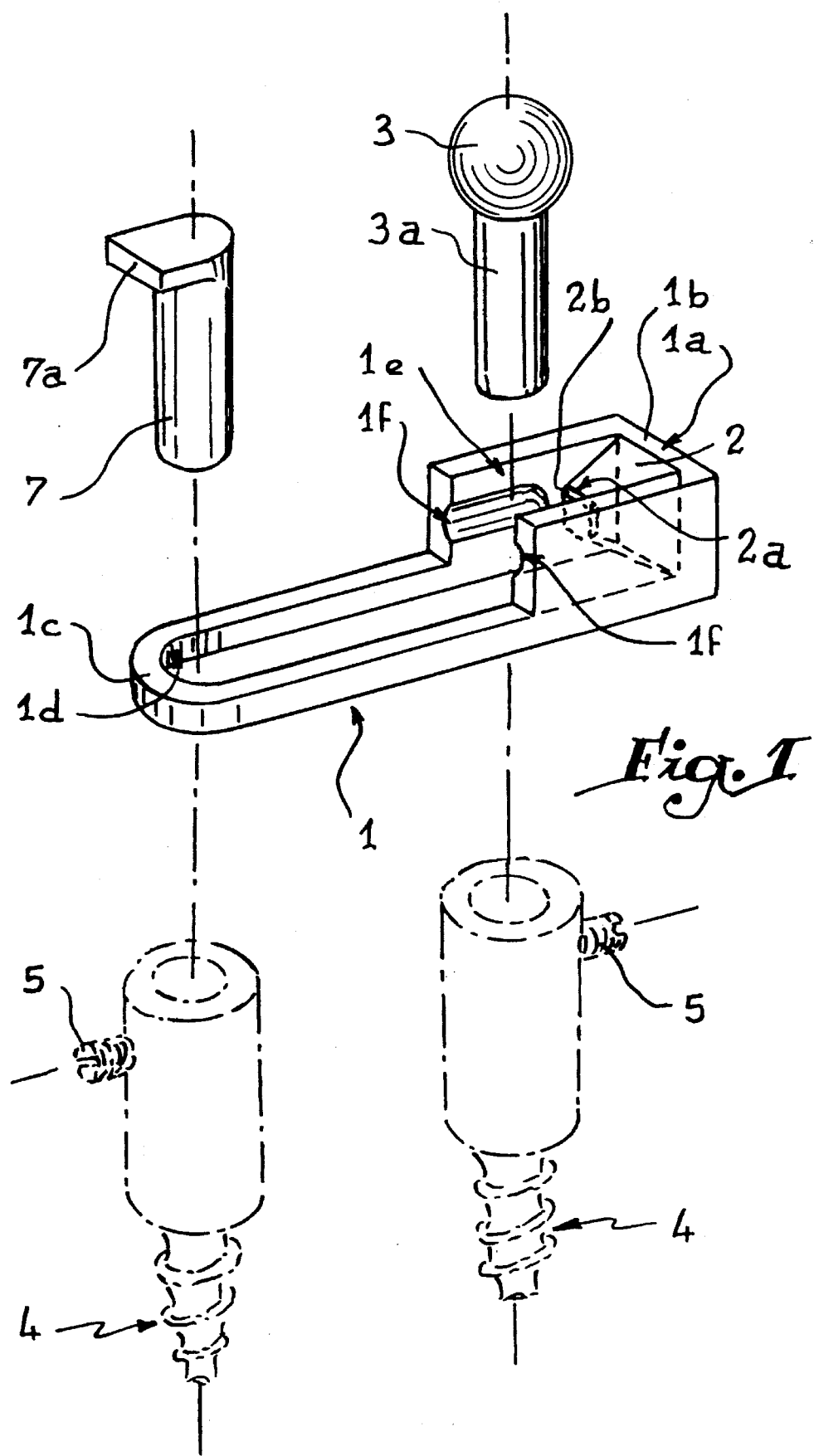
Fig. I

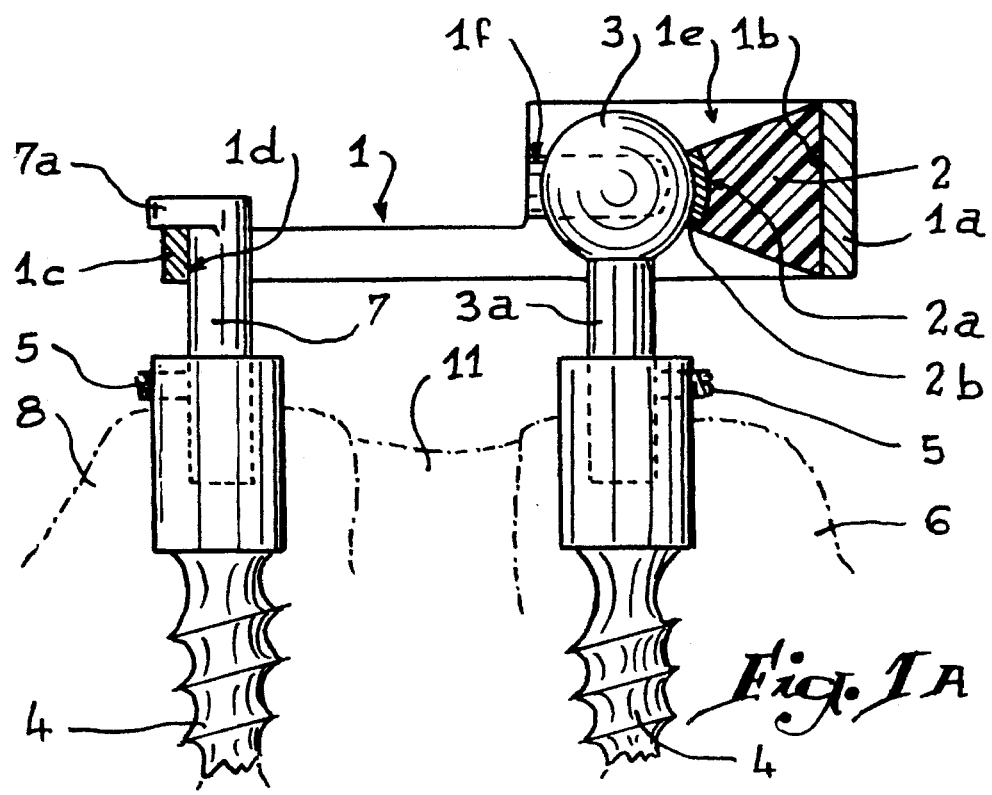
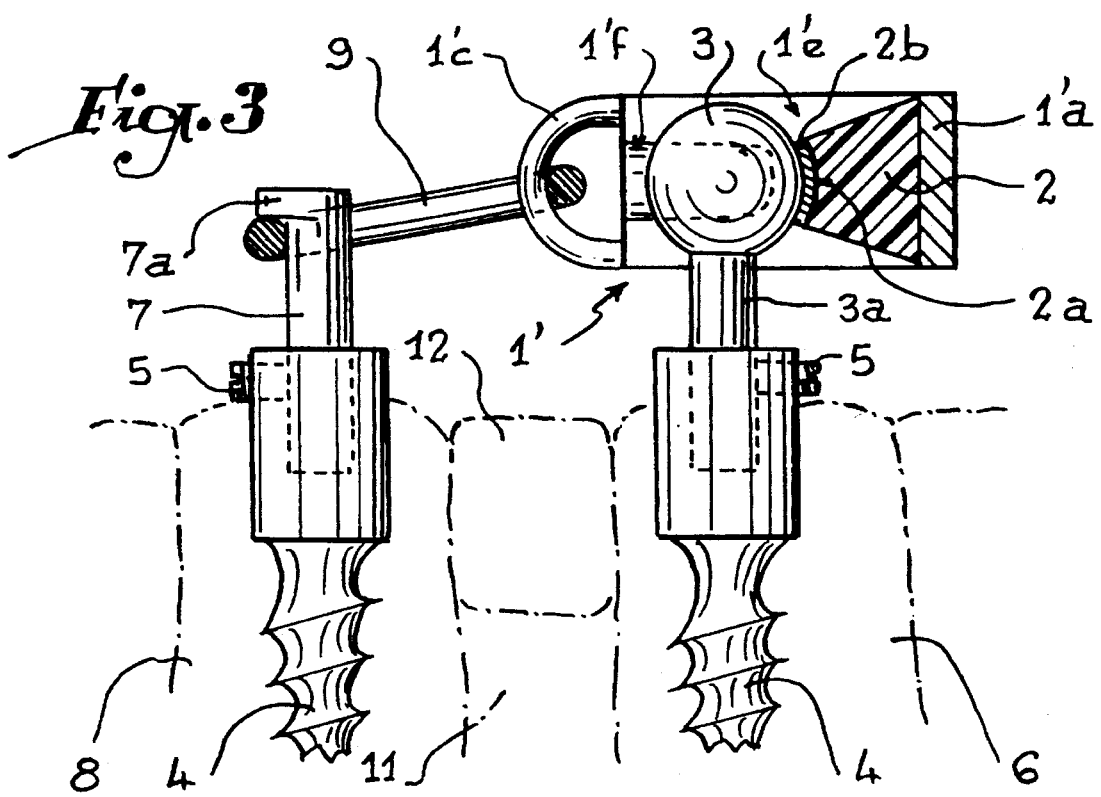

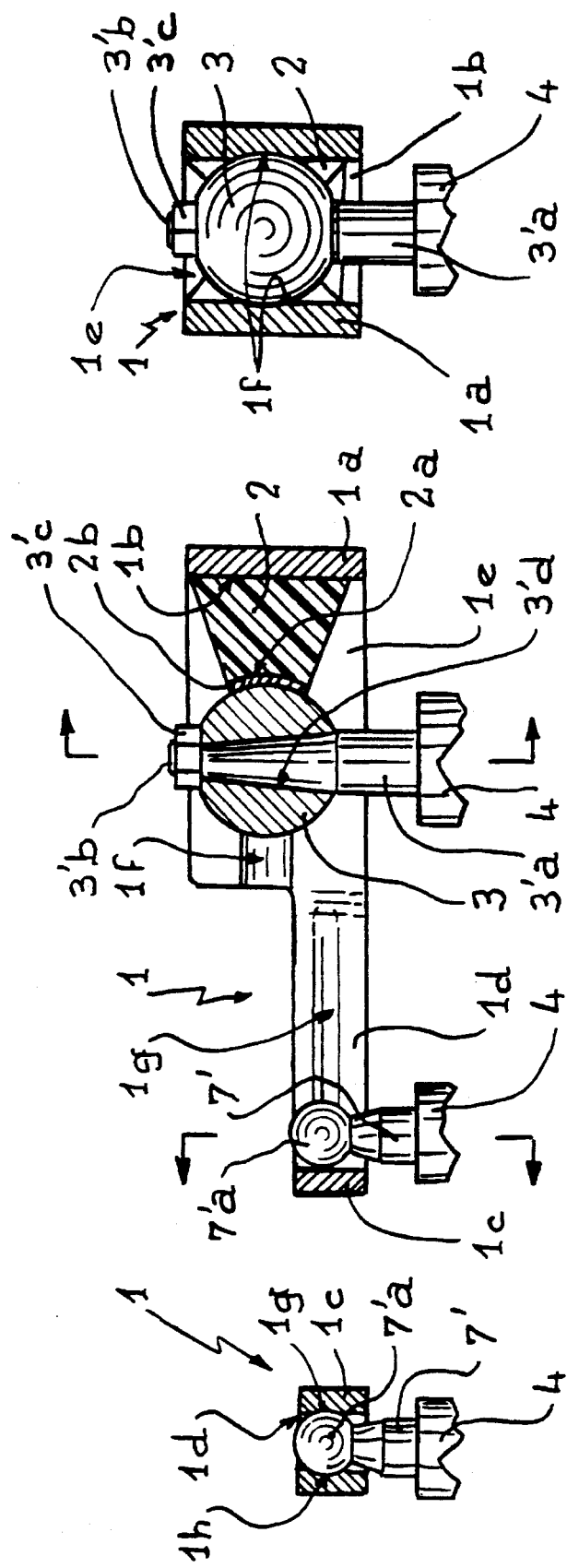

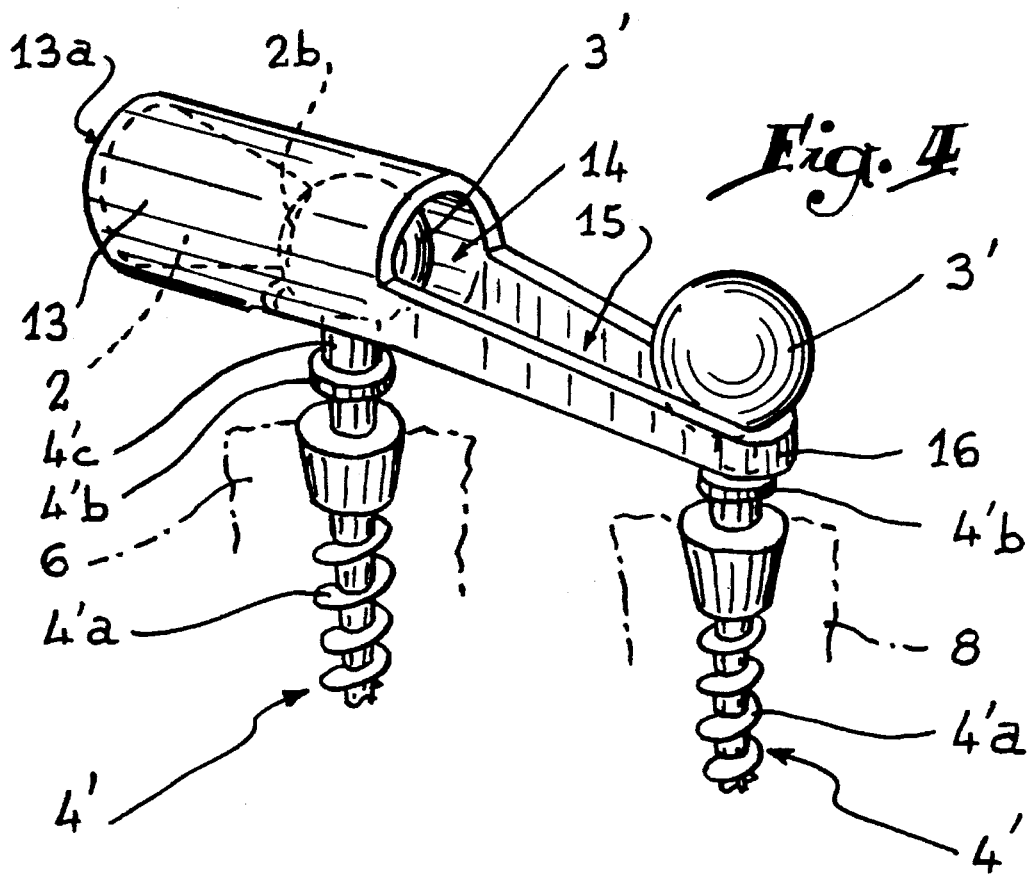
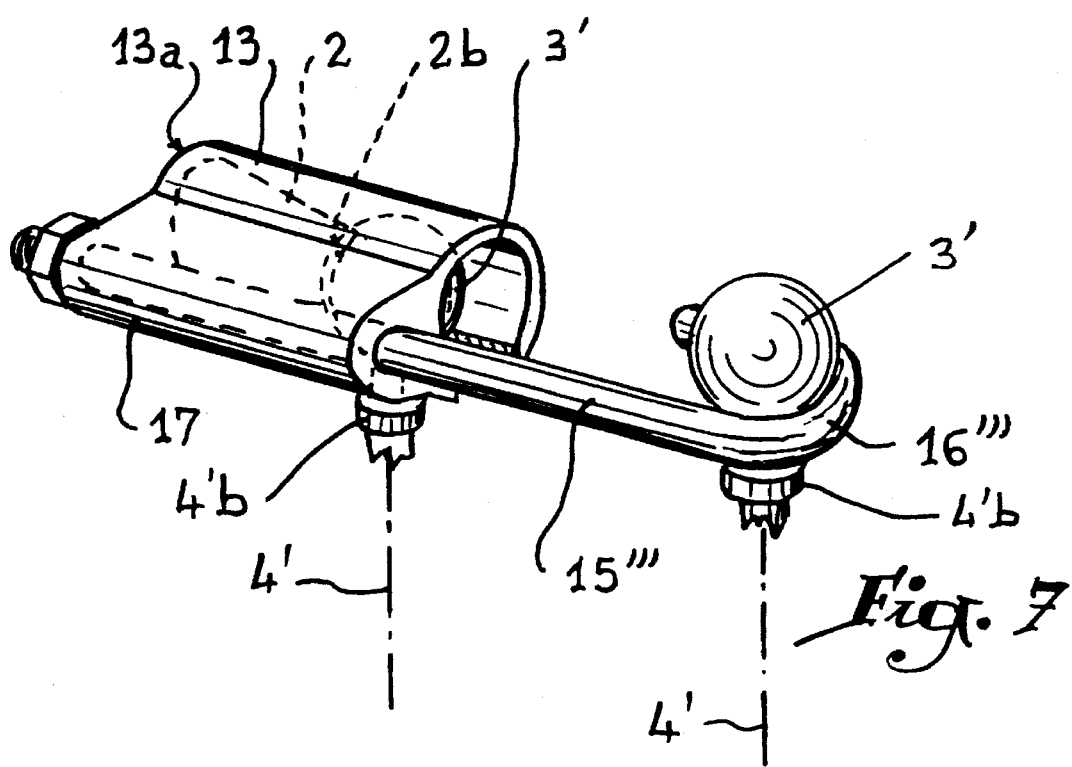

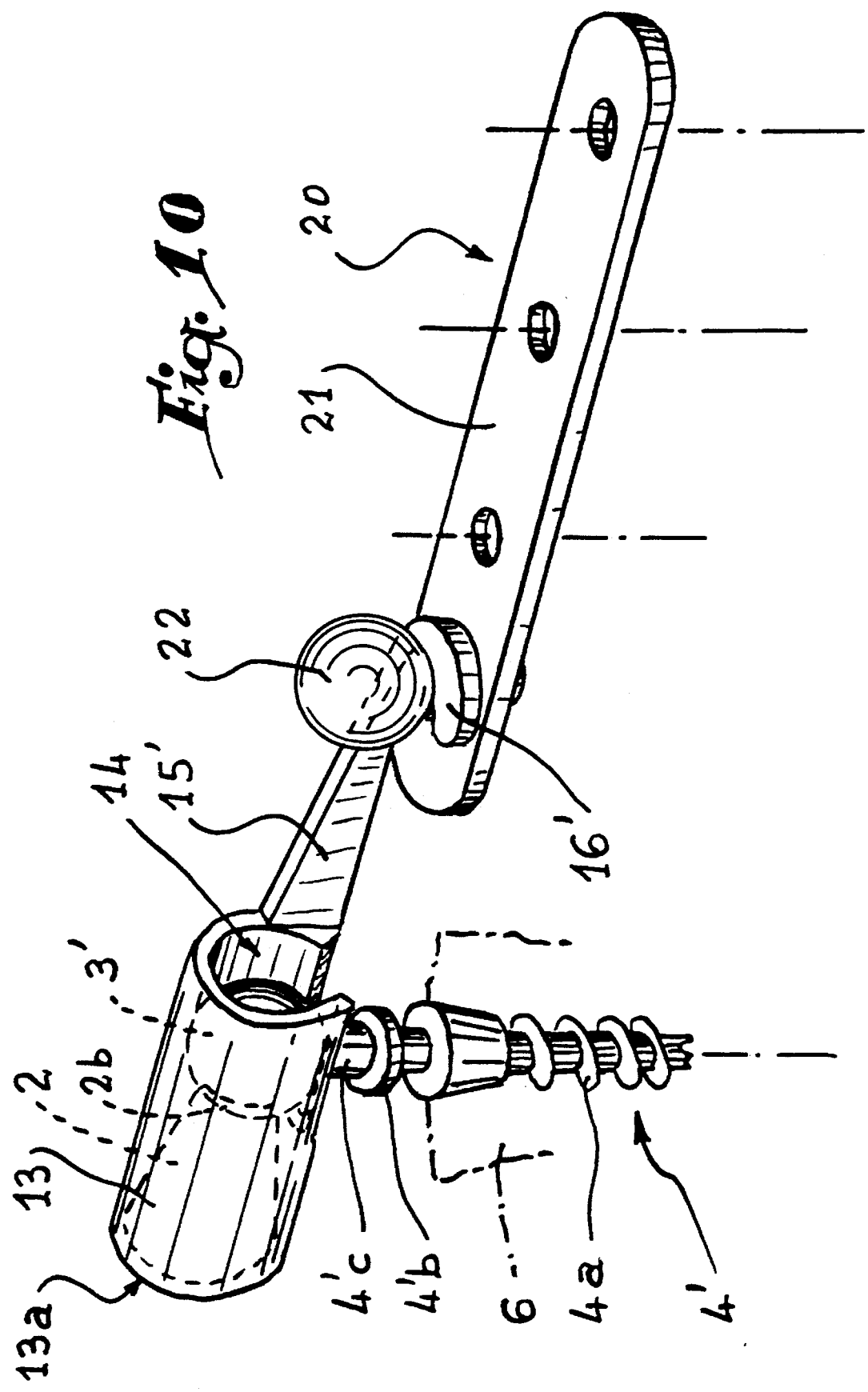

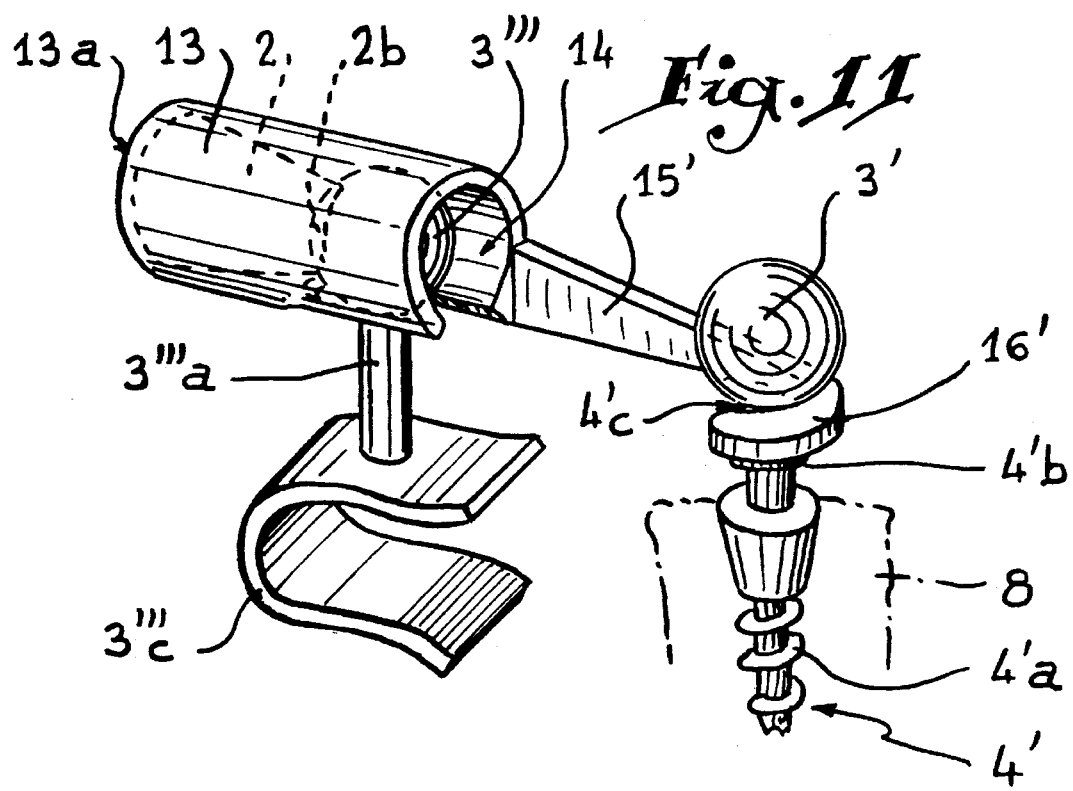
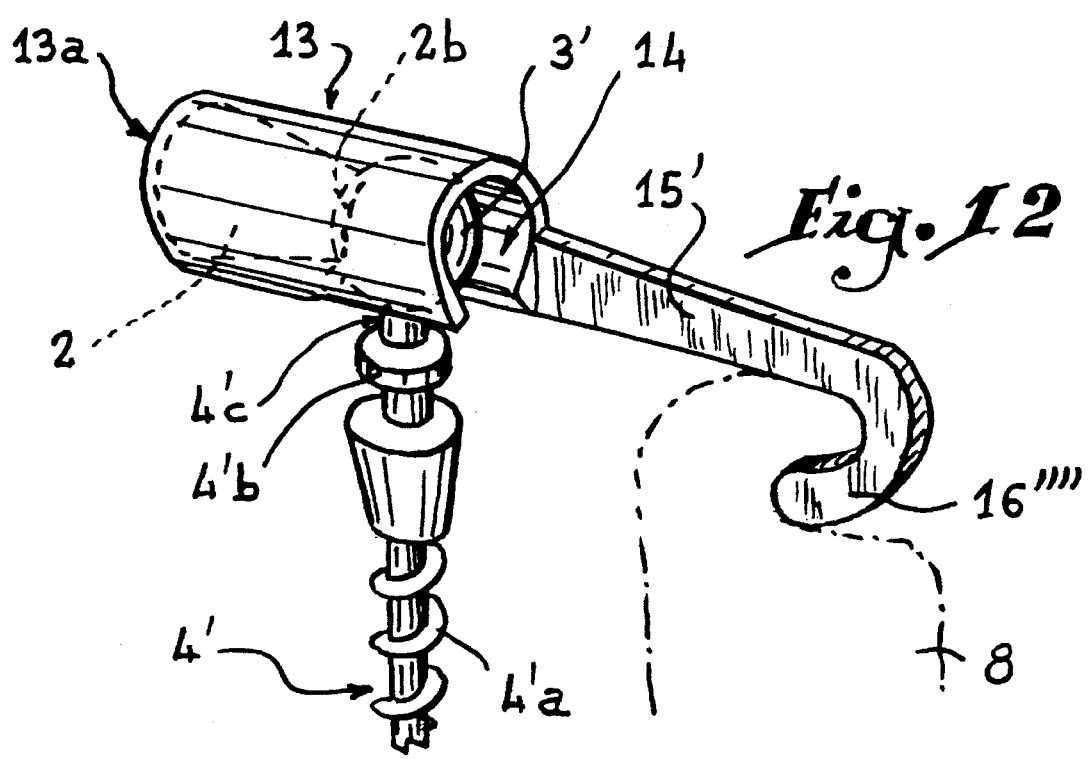

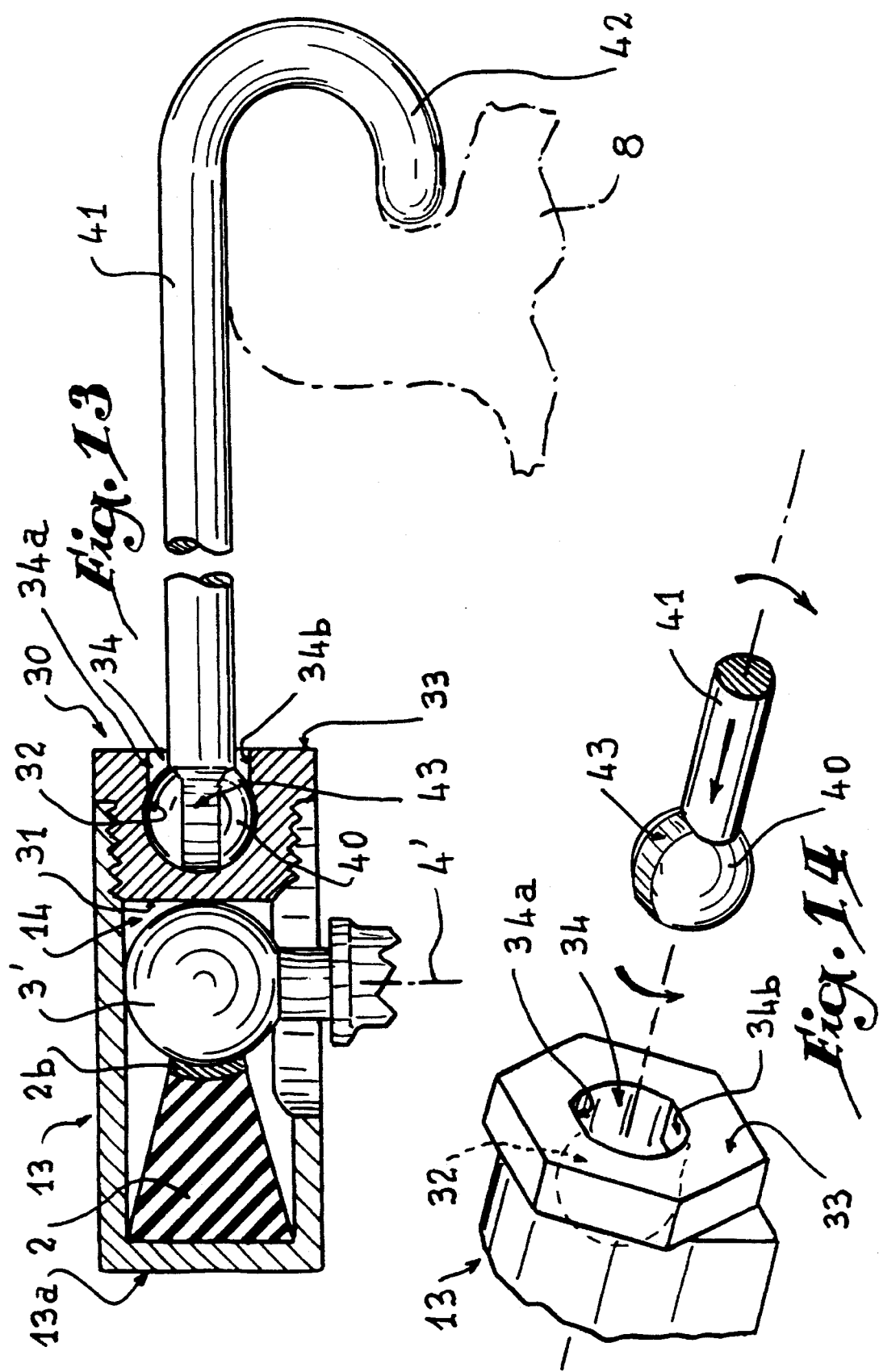

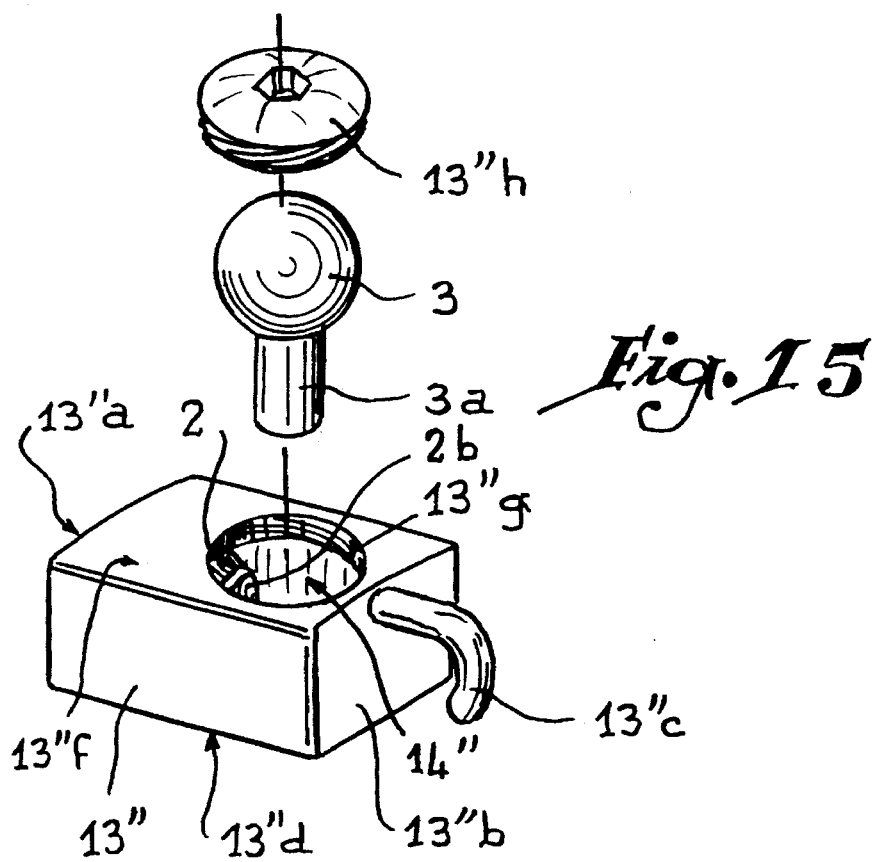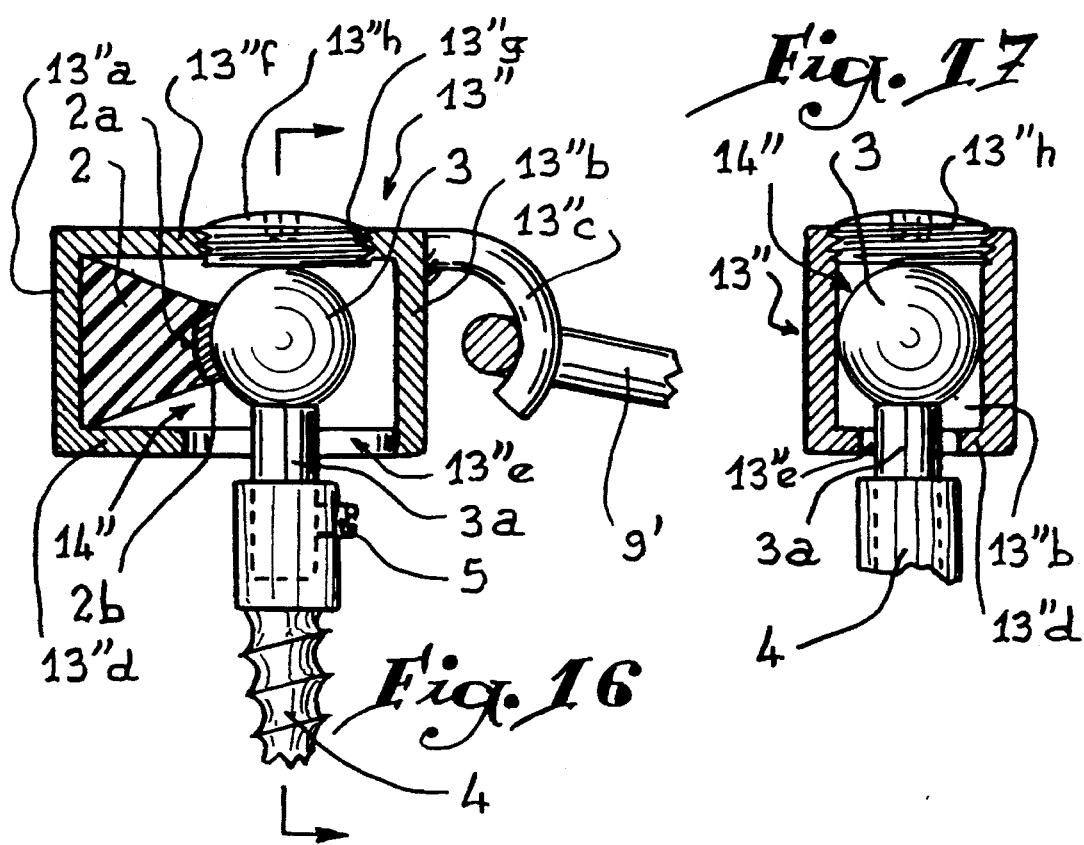

5,562,737

EXTRA-DISCAL INTERVERTEBRAL PROSTHESIS

BACKGROUND OF THE INVENTION

1. Field of the Invention

The present invention relates to an extra-discal intervertebral prosthesis implanted outside the disc of a patient's spine to compensate for defects of the spine.

2. History of the Related Art

Systems are known, comprising a ligament in the form of a ring associated with pedicular screws engaged in at least two adjacent vertebrae whose intervertebral disc presents a pathology. Such systems have the drawback of sometimes breaking under the action of the repeated forces of extension that they support, as they are made of textile. In addition, they cause fibroses, like all textiles implanted in the human body. This type of system imperfectly controls the variation in intervertebral flexion-extension and does not allow a precise approach of the vertebral repositioning and of the control of the residual movement between the two vertebrae.

The present invention aims at overcoming these drawbacks and at enabling an extra-discal intervertebral prosthesis better supported by the spine which does not present a risk of rupture and which precisely controls the residual movement in the direction of vertebral flexion and/or extension. Such control is that of the variation of the distance from one pedicle to the other of two adjacent vertebrae during the movement of flexion and/or extension.

SUMMARY OF THE INVENTION

To that end, the prosthesis according to the invention is made in the form of a totally or partially closed, elongated body comprising a compression chamber, one of the ends of the chamber being provided with an elastic block having a free face in abutment against a ball joint associated with a fixation means engaged in a vertebra. The body is connected directly or indirectly by at least one connecting means which is in abutment against a fixation means implanted in another vertebra.

In a preferred embodiment, the free face of the elastic block is in the form of a concave portion of sphere of the same diameter as the ball joint mentioned above. To protect this free face, a rigid shell having the form of a concave spherical dome may be added thereto.

According to a first embodiment, the end of the body opposite the one which carries the elastic block is in abutment against the stem of a hook secured to a fixation means implanted in the other vertebra.

It is also possible to connect to the hook the end of the body which is opposite the elastic block, by means of a link.

Finally, the invention also relates to the combination of a prosthesis as described hereinabove with an elastic shim engaged between the two vertebrae receiving pedicular screws, the shim replacing, for example, an injured part of the corresponding intervertebral disc.

BRIEF DESCRIPTION OF THE DRAWINGS

The invention will be more readily understood on reading the following description with reference to the accompanying drawings, in which:

FIGS. 1 and 1A are views showing the different elements of an extra-discal intervertebral prosthesis according to the invention.

FIGS. 2 to 2C are views similar to those of FIG. 1, but illustrating a first variant of the extra-discal intervertebral prosthesis.

FIG. 3 is a view similar to that of FIG. 2, but illustrating a second variant of the intervertebral prosthesis according to the invention.

FIGS. 4 to 6 are views in perspective showing several variants of the extra-discal intervertebral prosthesis according to the invention.

FIG. 7 is a view similar to that of FIG. 4, but illustrating an intervertebral prosthesis whose connecting rod may slide with respect to the body of said prosthesis.

FIG. 10 is a view showing the association of the intervertebral prosthesis according to the invention with a rod or plate of an osteosynthesis fixator.

FIG. 11 is a view showing a variant of the means for fixation of the intervertebral prosthesis in the vertebrae of a spine.

FIG. 12 is a view illustrating a variant hooking of the rods or plates on the adjacent vertebra to be joined.

FIGS. 13 and 14 are views representing a variant of the intervertebral prosthesis.

FIGS. 15 to 17 are views showing a last variant of an extra-discal intervertebral prosthesis.

DESCRIPTION OF PREFERRED EMBODIMENT

Figure 2:
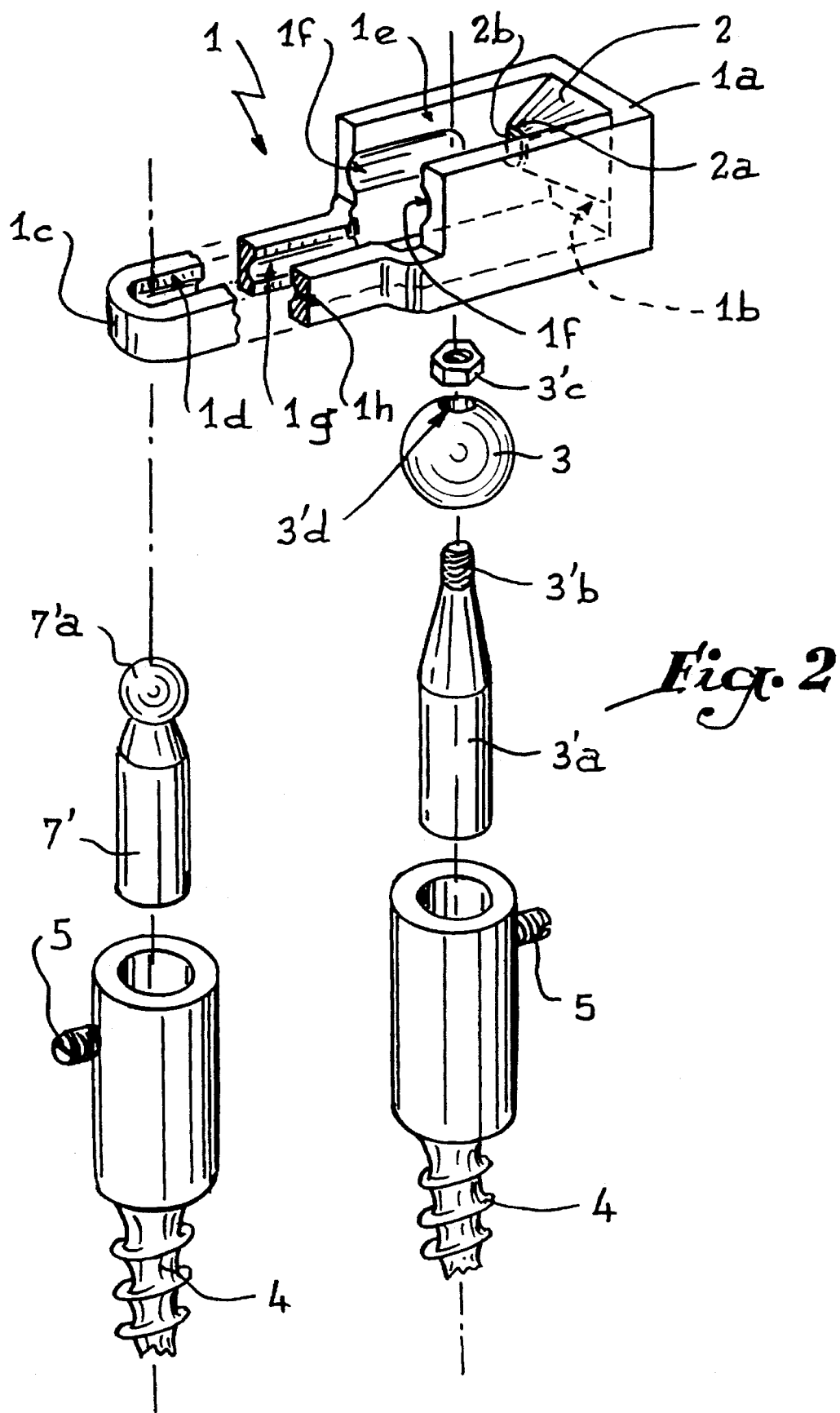

The prosthesis according to the invention, illustrated in FIGS. 1 and 1A, essentially comprises a rigid body 1, having an elongated and open form whose end 1a is made thicker so as to present a much greater height than the rest of the body in order to define a compression chamber 1e. The thickened end 1a of the chamber 1e forms and end bottom 1b which is preferably flat, but which might also be rounded. Against the bottom 1b there has been assembled, by any appropriate means, an elastic block 2 made for example of a natural or synthetic elastomer. The block preferably adheres against the bottom 1b of the end 1a of the body 1. The block 2 is advantageously made in the form of a frustum of pyramid, of which the free face 2a presents the form of a concave portion of sphere.

Face 2a is intended to cooperate closely with a ball joint 3 having a stem 3a assembled on a fixation means or a pedicular screw 4, for example, by a press screw 5, as is well known in the art. The means for fixation in the vertebrae may also be constituted by a hook which slides beneath the laminae of each vertebra to be connected, as will be seen more readily hereinafter. The screw 4 is, of course, implanted in the pedicle of one of the vertebrae 6 of a patient. Face 2a may be coated, as illustrated in FIG. 1A, with a rigid shell 2b which is concave and of diameter equal to that of the ball joint 3. Such a shell may be made of any appropriate material and more particularly stainless steel.

The walls of the compression chamber 1e extending perpendicularly to the bottom 1b respectively comprise an opening recess 1f. This recess has the form of a portion of circle of which the radius is equivalent to that of the ball joint 3 in order to retain the latter in its vertical displacements with respect to the body 1.

The second end 1c of the body 1, which has the form of a "U", is rounded so that its inner face 1d may come into close abutment against a cylindrical stem 7 associated with another pedicular screw 4 implanted in the vertebra 8 adjacent vertebra 6. The stem 7 advantageously includes a head 7a extending above the end 1c of the body 1, as is illustrated in FIG. 1A, with the result that this end 1c cooperates with a hook to prevent the body 1 from tipping outwardly with respect to the vertebra 8.

FIGS. 2 to 2C show a variant of the extra-discal intervertebral prosthesis shown in FIGS. 1 and 1A. The end 1c comprises on its inner face 1d two opposite recesses 1g and 1h which cooperate with a ball joint 7'a of small diameter secured to a stem 7'. The stem is fixed on the pedicular screw 4 in the same way as for stem 7. The recesses 1g and 1h present the profile of a portion of circle whose radius is identical to that of the ball joint 7'a so the joint is free in its horizontal displacements and retained in its vertical movements.

FIGS. 2 to 2C also show a variant of the ball joint 3 which may be connected to a stem 3'a of conical profile terminating in a threaded part 3'b which cooperates with a nut 3'c. The ball joint 3 has a hole 3'd of conical profile which cooperates with the stem 3'a, while the nut 3'c immobilizes the ball joint 3.

As illustrated in FIG. 3, the shape of the body referenced 1' may be changed so that its head 1'a, identical to that, 1a, of the body 1, is associated with a simple shackle 1'c corresponding to the end 1c of the body 1. The body 1' also comprises a compression chamber 1'e provided with a recess 1'f in which the elastic block 2 is fixed. Under these conditions, the connection between the ball joint 3 and the stem 7, i.e. between vertebrae 6 and 8, is completed by a link 9 surrounding the stem 7 and the shackle 1'c, the assembly of the ball joint 3 and of the body 1' remaining identical to that provided for the body 1.

Figure 5:
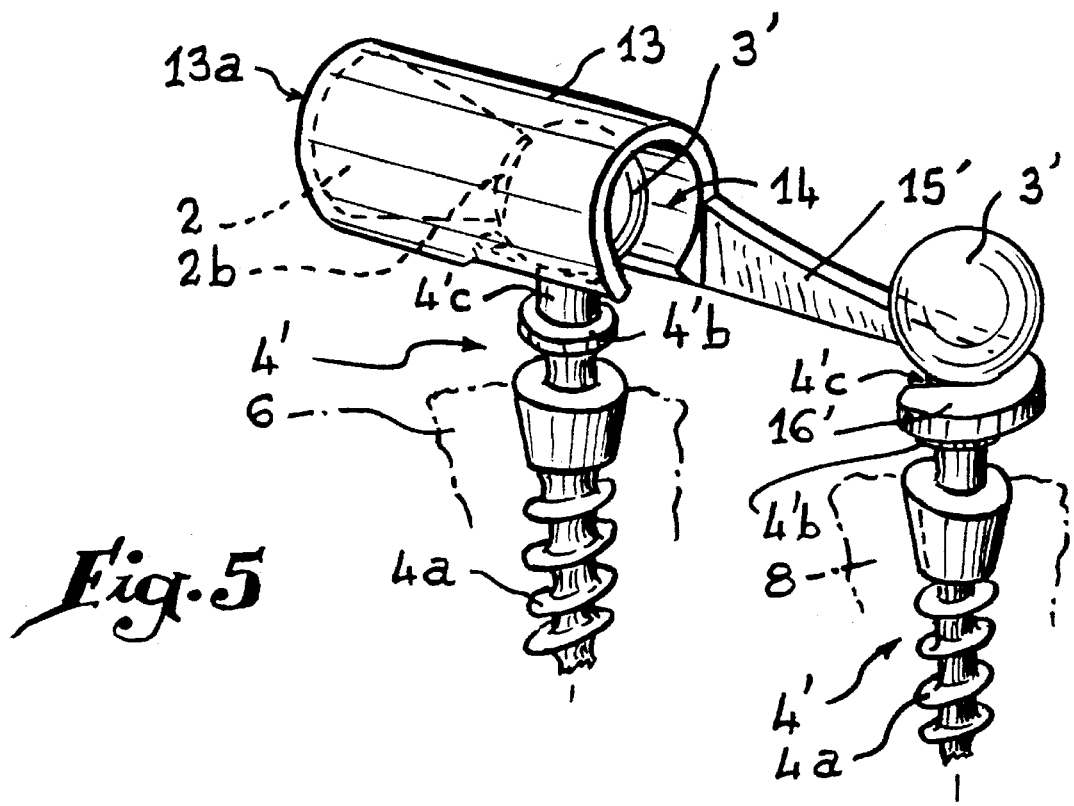
Figure 6:
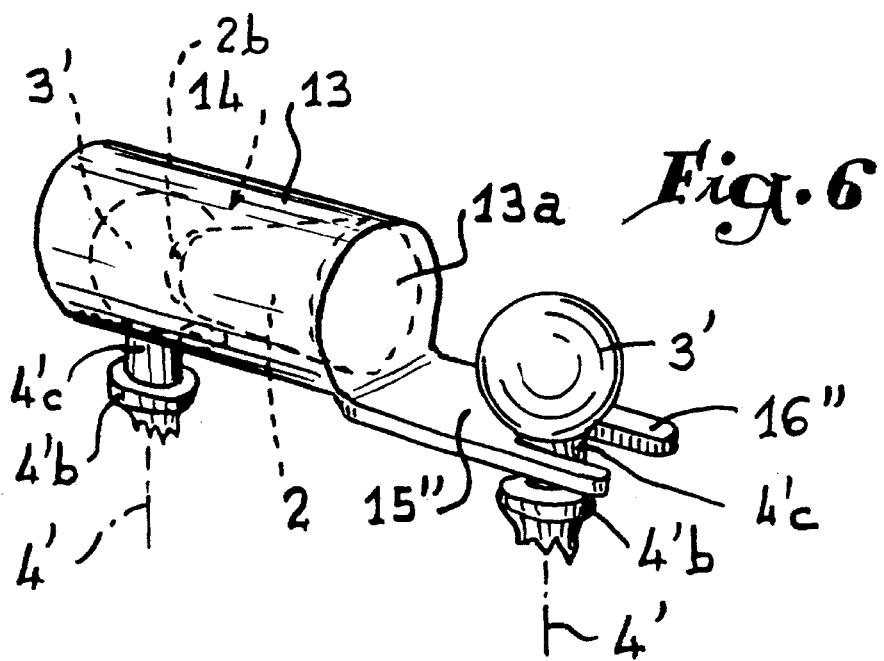

FIGS. 4 to 6 show preferred variants of the invention which consist in providing a cylindrical body 13 of which one of the ends is closed by a bottom 13a defining a compression chamber 14, while the opposite end is open for the positioning of a ball joint 3' secured to a pedicular screw 4' implanted in the vertebra 6. Against the bottom of the compression chamber 14 is fixed the elastic block 2 described hereinbefore so that its face 2a, secured to the shell 2b, cooperates closely with the ball joint 3' of the screw 4'.

Body 13 is secured at its open end with a stem 15 in the form of a "U" so that its rounded end 16 may come into close abutment against a pedicular screw 4' anchored in the adjacent vertebra 8 (FIG. 4).

The pedicular screw 4' comprises, above its threaded part 4'a, a circular stop 4'b which defines with the ball joint 3' a space 4'c for axial retention of the curved part 16 of the stem 15 (FIG.4).

The open end of the body 13 may be closed by a stopper or an envelope or a gusset (not shown) in order to avoid any penetration of living tissues located near the compression chamber 14.

A first variant of the embodiment shown in FIG. 4 consists of the body 13 being secured at its open end with a horizontal stem 15' in the form of a walking stick 15' comprising a curved part 15' in a horizontal plane which abuts against another pedicular screw 4' implanted in the adjacent vertebra 8 (FIG. 5).

FIG. 6 illustrates a second variant of the prosthesis 13 shown in FIG. 4, wherein the bottom 13a of the chamber 14 is secured on its outer face, in line with the body 13, with a rod 15" of flattened profile whose free end 16" is in the form of a fork.

Inside the body 13 and against the inner face of the bottom 13a of the chamber 14 is fixed an elastic block 2 whose face 2a which is secured to the shell 2b is intended to cooperate closely with the ball joint 3' of the pedicular screw 4' implanted in vertebra 6. The fork 16" of the rod 15" is provided to cooperate with the space 4'c of the pedicular screw 4' implanted in the vertebra 8 close to vertebra 6.

The body 13 shown in FIG. 6 functions strictly in opposite directions from those described hereinbefore. In fact, the elastic block 2 is compressed when the distance separating the two ball joints 3' of the adjacent pedicular screws 4' decreases.

FIG. 7 shows a variant of FIG. 4 wherein a rod 15'" is provided independent of body 13 and is adjustable in length with respect thereto. The rod 15'" slides inside a guide 17 secured along the body 13. Rod 15'" is retained towards the bottom 13a of the body 13 by a suitable stop system, such as for example a nut.

Rod 15'" comprises a curved end 16'" which cooperates with the free space 4'c of a screw 4'.

Figure 8:
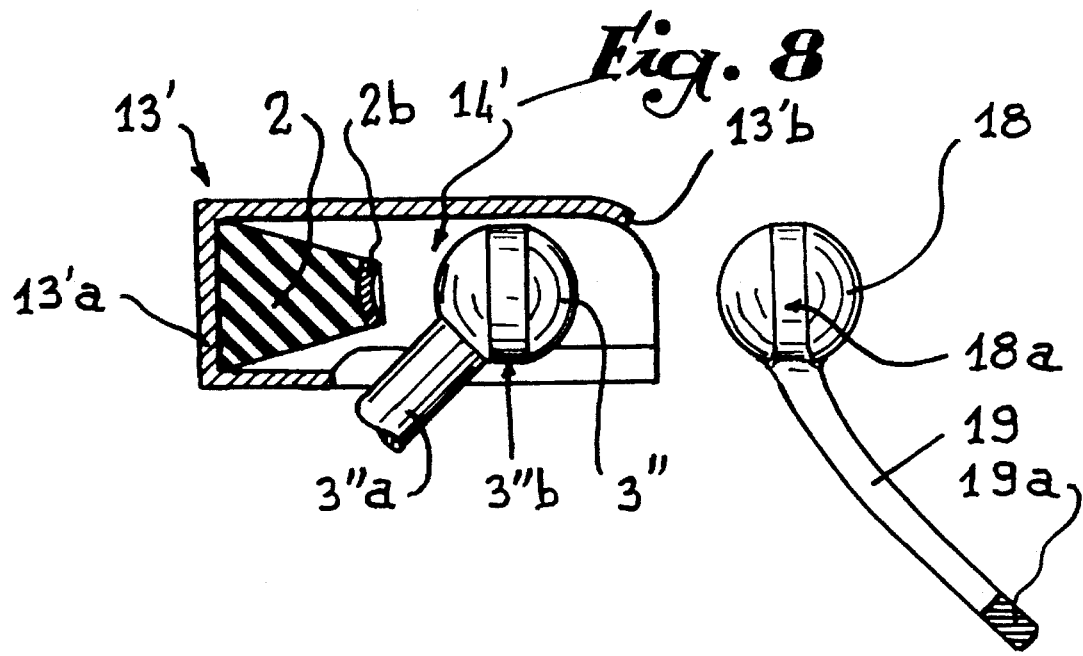
FIGS. 8 and 9 are sections illustrating another variant of the intervertebral prosthesis.
Figure 9:
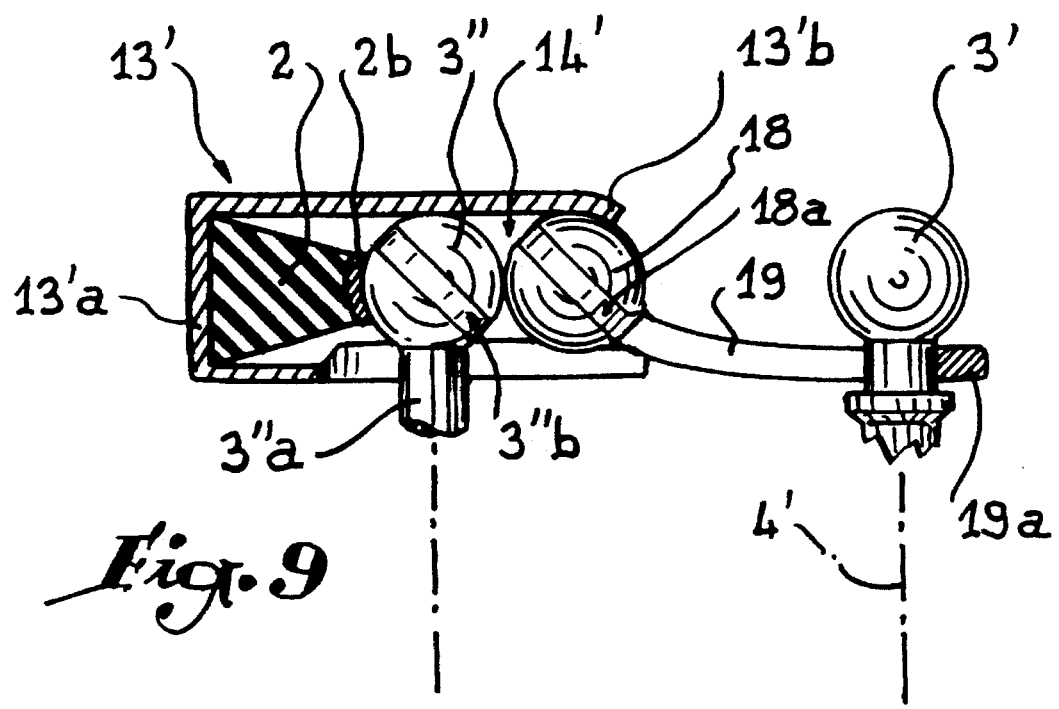

FIGS. 8 and 9 show a body 13' comprising a compression chamber 14' of which one of the ends is closed by a bottom 13'a, while the opposite end is open and has a deformation 13'b forming a stop and reducing the inlet section of the chamber 14'.

Inside the body 13', the elastic block 2 is fixed against its bottom 13'a so that the shell 2b cooperates closely with a ball joint 3" which is secured to a stem 3"a cooperating for example with a pedicular screw 4 with the aid of a press screw 5, as shown in FIG. 1.

Ball joint 3'" presents an equatorial flat portion 3"b allowing the introduction of the ball joint in the chamber 14'. The flat portion 3"b requires a surgeon to introduce the ball joint 3" in the position shown in FIG. 8, and then pivot the ball joint 3" about its axis for the stem 3"a to be in a vertical position (FIG. 9).

It will be understood that, in this position, the ball joint 3" is retained within the chamber 14' of the body 13'.

A second ball joint 18 comprises an equatorial flat portion 18a allowing its introduction in the chamber 14'. In the same way as for the ball joint 3", ball joint 18 is introduced in the position shown in FIG. 8 and then pivoted to the position of FIG. 9 in order to be retained inside the chamber 14' by the deformation 13'b of the body 13'. The flat portion 18a presents a diameter identical to that, 3"b, of ball joint 3".

Ball joint 18 is secured to a horizontal plate 19 or rod which includes at its free end 19a, i.e. opposite the ball joint, either a curved part or a fork or an appropriate anchoring system depending on the use of the body 13'.

The free end of the plate 19 s provided to cooperate with the space 4'c of another screw 4' implanted in the vertebra 8 adjacent vertebra 6.

The different variants described hereinbefore may be associated with one another to constitute an extra-discal intervertebral prosthesis having the quality of damping the displacements between vertebrae 6 and 8 in compression and in extension, permanently.

It will be noted that the different bodies shown in FIGS. 1 to 8 may be combined with a rod or plate 21 of an osteosynthesis fixator 20 to constitute an assembly for protecting the ends of a rigid system, thus avoiding too great a concentration of stresses on certain stages. The rod or plate 21 comprises at one of the free ends a retaining element 22 which cooperates with the connecting means 9, 15, 15', 15", 15'", 19 of the different protheses described hereinbefore (FIG. 10). In our example, the extra-discal intervertebral prosthesis shown is that of FIG. 5. All the other variants may, of course, be provided without changing the combination.

FIG. 11 shows a variant of the means for fixation in the vertebrae 6 and 8. In fact, the ball joint 3''', by its stem 3'''a, may be secured to a hook 3'''c which hooks directly on the laminae of the vertebrae to be connected, thus producing a sub-lamina anchoring device.

FIG. 12 shows a variant of that of FIG. 5 of which the end of the rod 15' is curved in the form of a hook 16'''' in a vertical plane, hooking directly beneath an osseous lamina of the adjacent vertebra 8 to be connected.

FIGS. 13 and 14 illustrate a variant of the one shown in FIGS. 8 and 9. The extra-discal prosthesis comprises a rigid body 13 of cylindrical profile, of which the bottom 13a of the chamber 14 receives the elastic block 2. The block is secured to a shell or the like 2b which is intended to cooperate closely with the ball joint 3' associated with a pedicular screw 4'. The end opposite the bottom 13a of the body 13 is closed by a threaded stopper 30 which makes it possible to render the chamber 14 tight when the screw 4' is associated with a sealing gusset (not shown). The stopper 30 has a rear face 31 which comes into abutment against the ball joint 3' so as to maintain the latter axially inside the chamber 14. Inside the stopper 30 is a spherical housing 32 which opens out on the front face 33 opposite the rear face 31 through an opening 34.

The opening 34 has a cylindrical profile provided with two opposite, parallel, flat portions 34a and 34b separated from each other by a distance less than the diameter of the spherical housing 32 (FIG. 14).

The diameter of the cylindrical opening 34 is equal to those of the spherical housing 32 and of the ball joint 40.

Inside the housing 32 is retained a ball joint 40 secured to a rod 41 of which the free end 42 is in the form of a hook, cooperating directly beneath the osseous lamina of an adjacent vertebra 8. The free end 42 may, of course, take other shapes, such as for example a fork or a hook, cooperating with a pedicular screw (not shown).

The ball joint 40 comprises an equatorial flat portion 43 whose diameter is substantially equivalent to the distance separating the flat portions 34a and 34b of the opening 34. It is observed that the flat portion 43 of the ball joint 40 which allows the introduction of the joint inside the spherical housing 32, is machined in a plane perpendicular to that of hooking free end 42 (FIG. 13).

In fact, the surgeon orients the ball joint 40 so that the flat portion 43 corresponds with those 34a and 34b for positioning it inside the stopper 30. This position allows the introduction of the ball joint, while, for retention thereof, it suffices to pivot the ball joint 40 through a quarter turn so its spherical part comes into abutment against the flat portions 34a and 34b separated by a distance less than the diameter of the ball joint 40 (FIG. 13).

FIGS. 15 to 17 show a last variant of the extra-discal intervertebral prosthesis which comprises a rigid body 13" of which the bottom 13"a of the chamber 14" receives the elastic block 2. The end opposite the bottom 13"a of the body 13" is closed by a wall 13"b whose outer face is secured to a shackle 13"c which may be open or closed. The shackle may be disposed in a plane which is vertical or horizontal. The lower face 13"d of the body 13" connecting the bottom 13"a and the wall 13"b has a slot 13"e opening inside the chamber 14". Opposite the slot 13"e, the upper face 13"f of the body 13" has a threaded hole 13"g for the passage for example of the ball joint 3 secured to the rod 3a which is mounted to a screw 4 previously fixed in a vertebra (not shown).

The threaded hole 13"g presents a diameter greater than that of the ball joint 3 to allow it to be positioned inside the chamber 14". The ball joint 3' is disposed in the chamber 14" to bear against the shell 2b of the elastic block 2, while the rod 3a cooperates with the slot 13"e.

The threaded hole 13"g receives a threaded stopper 13"h to close the chamber 14" when the ball joint 3 is introduced. The rod 3a may receive a bush (not shown) to render the chamber 14" completely tight.

The shackle 13"g is provided to cooperate with a link 9 of any shape connecting the body 13" to another screw 4 or 4' anchored to another vertebra.

It is observed that the rods 15, 15', 15", 15''' and 41 and the plate 19 are in the form either of a hook or a fork which are capable of coming into abutment against a pedicular screw 4, 4' or of anchoring directly in the bone or beneath the laminae of the vertebrae to be connected.

It will be noted that the elastic block 2 may take any shape without changing its characteristics. Moreover, the elastic block 2 may be associated with a spring (not shown) to improve its elastic characteristics. In addition, the material constituting the block 2 may vary depending on the desired elastic conditions and be combined with composite fibers, for example.

Finally, should the intervertebral disc 11 located between the vertebrae 6 and 8 have partially subsided, an elastic shim 12 of any shape may be added thereto, re-establishing a more normal spacing between the vertebrae and which would act in combination with the extra-discal intervertebral prosthesis (FIG. 3).

What is claimed is:

1. An extra-discal prosthesis comprising:
   a means for attaching the prosthesis onto two vertebrae of a spine of a patient, said means for attaching including first and second fixation means adapted to engage the two vertebrae;
   a body having a first end and a second end, said body being at least partially closed and including a compression chamber having an elastic block at said first end;
   a ball joint in abutment with a free face of said elastic block, said ball joint engaging said first fixation means; and
   a connection means extending from said body and engaging said second fixation means.

2. The prosthesis of claim 1, wherein said ball joint has a first diameter, said free face of said elastic block being in the form of a concave segment of sphere having a diameter the same as said first diameter.

3. The prosthesis of claim 2, wherein said free face of said elastic block includes a rigid shell having the form of a concave spherical dome having a diameter equal to that of said first diameter.

4. The prosthesis of claim 1, wherein said second end of said body is in abutment against said connection means, said connection means being a rod in the form of a hook which is secured to said second fixation means.

5. The prosthesis of claim 4, wherein said rod comprises a head extending above said second end of said body.

6. The prothesis of claim 1, wherein said second end of said body is connected to said connection means, said connection means being in the form of a link.

7. The prosthesis of claim 1, wherein said connection means includes a rod comprising an end which abuts against said second fixation means.

8. The prothesis of claim 7, wherein said end of said rod is in the shape of a U.

9. The prosthesis of claim 7, wherein said end of said rod is curved.

10. The prosthesis of claim 7, wherein said rod is in a flattened profile, said end being shaped as a fork for engaging said second fixation means.

11. The prosthesis of claim 7, wherein said end of said rod is curved.

12. The prosthesis of claim 7, wherein said body includes a guide in which said rod slides, and means for retaining said rod within said guide.

13. The prosthesis of claim 1, wherein said body is generally cylindrical and said second end is open, said connection means includes a second ball joint which is received within said compression chamber and which abuts against said ball joint, said second ball joint being secured to a plate which has a free end adapted to engage said second fixation means.

14. The prosthesis of claim 13, wherein said second end of said body tapers inwardly to form a stop.

15. The prosthesis of claim 14, wherein said ball joint and said second ball joint each include an equatorial flat portion and each being configured to be receivable through said second end into said compression chamber.

16. The prosthesis of claim 1, in combination with an elastic shim positioned between said first and second fixation means.

17. The prosthesis of claim 1, wherein said connection means is combined with an osteosynthesis fixator.

18. The prosthesis of claim 1, including means to prevent penetration into said body of living tissues located near the compression chamber.

19. The prosthesis of claim 1, wherein said first fixation means is a pedicular screw, said ball joint including a rod receivable within said pedicular screw constituting said first fixation means.

20. The prosthesis of claim 1, wherein said second fixation means is constituted by a pedicular screw, a stem extending from said pedicular screw and a head extending from said stem.

21. The prosthesis of claim 1, wherein said first fixation means includes a hook and a stem, said ball joint being mounted to said stem.

22. The prosthesis of claim 1, wherein said second fixation means includes a curved end extending from said connection means.

23. The prosthesis of claim 1, wherein said second end of said body is closed by a stopper having a socket for retaining said connection means.

24. The prosthesis of claim 23, wherein said stopper comprises a face which abuts against said ball joint and said socket having two opposite, parallel, flat portions.

25. The prosthesis of claim 24, wherein said connection means includes a rod having a second ball joint, said second ball joint having an equatorial flat portion to allow introduction thereof in said socket.

26. The prothesis of claim 25, wherein said flat portion of said second ball joint is machined along a plane perpendicular to a hook portion of said rod.

27. The prosthesis of claim 1, wherein said elastic block includes a spring.

28. The prosthesis of claim 1, wherein said body includes upper and lower walls, said lower wall having a slot and said upper wall having a threaded hole for positioning said ball joint inside said compression chamber.

29. The prosthesis of claim 28, wherein a stopper is seated within said hole.

30. The prosthesis of claim 1, wherein said compression chamber includes opposite recesses for retaining said ball joint.

31. The prosthesis of claim 1, wherein said second end of said body is provided with two opposite recesses, said second fixation means including a ball joint secured to a rod which is mounted to a pedicular screw.

32. The prosthesis of claim 1, wherein said ball joint is mounted on a stem of conical profile, and a nut for retaining said ball joint an said stem.

* * * * *